United States Patent
Kawashima et al.

(10) Patent No.: US 7,143,454 B2
(45) Date of Patent: Dec. 5, 2006

(54) SWIMMING GOGGLES

(75) Inventors: Haruo Kawashima, Tokyo (JP); Taro Fujima, Tokyo (JP)

(73) Assignee: Tabata Co., Ltd., Tokyo (JP)

( * ) Notice: Subject to any disclaimer, the term of this patent is extended or adjusted under 35 U.S.C. 154(b) by 86 days.

(21) Appl. No.: 10/995,426

(22) Filed: Nov. 24, 2004

(65) Prior Publication Data
US 2005/0120468 A1   Jun. 9, 2005

(30) Foreign Application Priority Data
Dec. 5, 2003   (JP)   ............................. 2003-407496

(51) Int. Cl.
  *A61F 9/02*   (2006.01)
(52) U.S. Cl. ............................................ 2/440; 2/445
(58) Field of Classification Search .................... 2/440, 2/441, 444, 445
See application file for complete search history.

(56) References Cited

U.S. PATENT DOCUMENTS

| | | | | |
|---|---|---|---|---|
| 4,755,040 A | * | 7/1988 | Haslbeck | 351/43 |
| 5,650,866 A | * | 7/1997 | Haslbeck | 351/43 |
| 6,029,284 A | * | 2/2000 | Kawashima et al. | 2/428 |
| 6,243,882 B1 | * | 6/2001 | Kawashima et al. | 2/428 |
| 6,253,387 B1 | * | 7/2001 | Yu | 2/428 |
| 6,721,963 B1 | * | 4/2004 | Kawashima | 2/426 |

FOREIGN PATENT DOCUMENTS

| | | |
|---|---|---|
| JP | 61-46498 | 12/1986 |
| JP | 3048517 | 2/1998 |

* cited by examiner

*Primary Examiner*—Katherine Moran
(74) *Attorney, Agent, or Firm*—Clark & Brody

(57) ABSTRACT

Swimming goggles includes lens assemblies and pad assemblies attached to peripheral frames of the respective lens assemblies. Each of the pad assemblies is formed by a first elastic member made of first elastic material which is relatively stiff and a second elastic member made of second elastic material which is relatively flexible wherein the second elastic member is in close contact with and bonded to the first elastic member in a radial direction of the lens assembly.

4 Claims, 5 Drawing Sheets

SWIMMING GOGGLES

BACKGROUND OF THE INVENTION

The present invention relates to swimming goggles.

In swimming goggles, it is well known to provide a pad made of a flexible elastic material around the peripheral frame of the lens assembly.

For example, in the case of the goggles disclosed in Japanese Utility Model Application Publication No. 1986-46498 (Citation 1), a tubular main body molded from hard plastic material is provided at one end with a lens assembly and at the other end with a flexible contact cushion made of sponge or the like. The flexible contact cushion comes in close contact with the wearer's face as such goggles are worn.

The swimming goggles' pad disclosed in Japanese Utility Model Registration No. 3048517 (Citation 2) comprises two different members of which the one is a face contacting layer and the other is a flexible layer. The face contacting layer comprises a shock absorbing segment attached to a lens frame and an extensional segment to which the flexible layer is attached. The face contacting layer presents a J-shaped cross-section and the flexible layer made of flexible material such as sponge is placed upon a distal end portion of this J-shaped cross-section in a thickness direction (i.e., back-and-forth direction) of the lenses.

The pad described in Citation 2 is advantageous in that two members being different in flexibility are combined to enhance a bonding effect between the pad and the lens frame, on one hand, and to ensure flexible and close contact with the wearer's face, on the other hand. Compared to the flexible contact cushion forming the pad described in Citation 1, the pad described in Citation 2 is certainly more advantageous. However, in the case of the pad described in Citation 2 comprising a combination of these two members, the flexible layer is placed on and bonded to the extensional segment of the face contacting layer in the back-and-forth direction of the goggles. To enhance the bonding effect between these extensional segments and the flexible layer, it is required not only to use adhesive having a high adhesive strength but also to enlarge the surface area over which these segment and layer are bonded to each other. However, enlargement of the bonded surface leads to enlargement of the outer diameter of the extensional segment and to the corresponding increase in a frictional resistance of water.

SUMMARY OF THE INVENTION

In view of the problem as has been described above, it is an object of the present invention to improve the swimming goggles in which each of the pad assemblies attached to the peripheral frames of the respective lens assemblies comprises two types of elastic members being different from each other in stiffness as well as color tone so that these two different types of elastic members can be non-detachably bonded to each other without increasing a frictional resistance of water.

The object set forth above is achieved, according to the present invention, by swimming goggles having a vertical direction, a transverse direction orthogonal to said vertical direction and a back-and-forth direction orthogonal to both the vertical direction and the transverse direction, the swimming goggles comprising a pair of cup-shaped lens assemblies arranged side by side in the transverse direction, annular pad assemblies attached peripheral frames of respective the lens assemblies and extending in the back-and-forth direction, a bridge extending between inner ends of the respective lens assemblies opposed to each other and a head strap assembly between outer ends of the respective lens assemblies, wherein the lens assemblies are formed by hard plastic material and each of the pad assemblies is formed from two types of elastic material of which the one defines a first elastic member non-detachably attached to each of the peripheral frames and the other defines a seconded elastic member non-detachably bonded to the first elastic member and destined to come in close contact with face of a swimmer wearing the swimming goggles.

The swimming goggles further comprises the following.

The first elastic members is formed from first elastic material and in close contact with and non-detachably bonded to the lens assembly in a radial direction of the lens assembly inclusive of the vertical direction and the transverse direction and in the back-and-forth direction, at least in the radial direction while the second elastic member is formed from second elastic material differing from the first elastic material in stiffness and any one of color tone and chemical composition and in close contact with and non-detachably bonded to the first elastic member in the radial direction and the back-and-forth direction, at least in the radial direction.

According to one preferred embodiment of the present invention, the first elastic material and the second elastic material constituting together to form the pad assembly extend between the inner ends of the respective lens assemblies to form the bridge.

According to another preferred embodiment of the present invention, the second elastic material is more flexible than the first elastic material.

The swimming goggles according to the present invention allow the area over which the first and second elastic members are bonded to each other to be enlarged without correspondingly enlarging the outer diameters of the lens assemblies as well as of the pad assemblies and therefore without increasing a frictional resistance of water. This is for the reason that the second elastic member is in close contact with and bonded to the first elastic member in the radial direction of the lens assemblies. In addition, the bridge is molded integrally with the pad assemblies according to the present invention and this measure is effective to alleviate a troublesome process for assembling the goggles as has been the case in which the bridge is prepared separately of the lens assemblies and the pad assemblies. Furthermore, the present invention adopts relatively flexible material as the second elastic material forming the second elastic member and places this second elastic material so as to face the wearer's nose and thereby to eliminate the anxiety that the bridge might uncomfortably compress the nose as the bridge comes in contact with the wearer's nose.

DETAILED DESCRIPTION OF THE PREFERRED EMBODIMENTS

Details of swimming goggles according to the present invention will be more fully understood from the description given hereunder with reference to the accompanying drawings.

Figure 1:
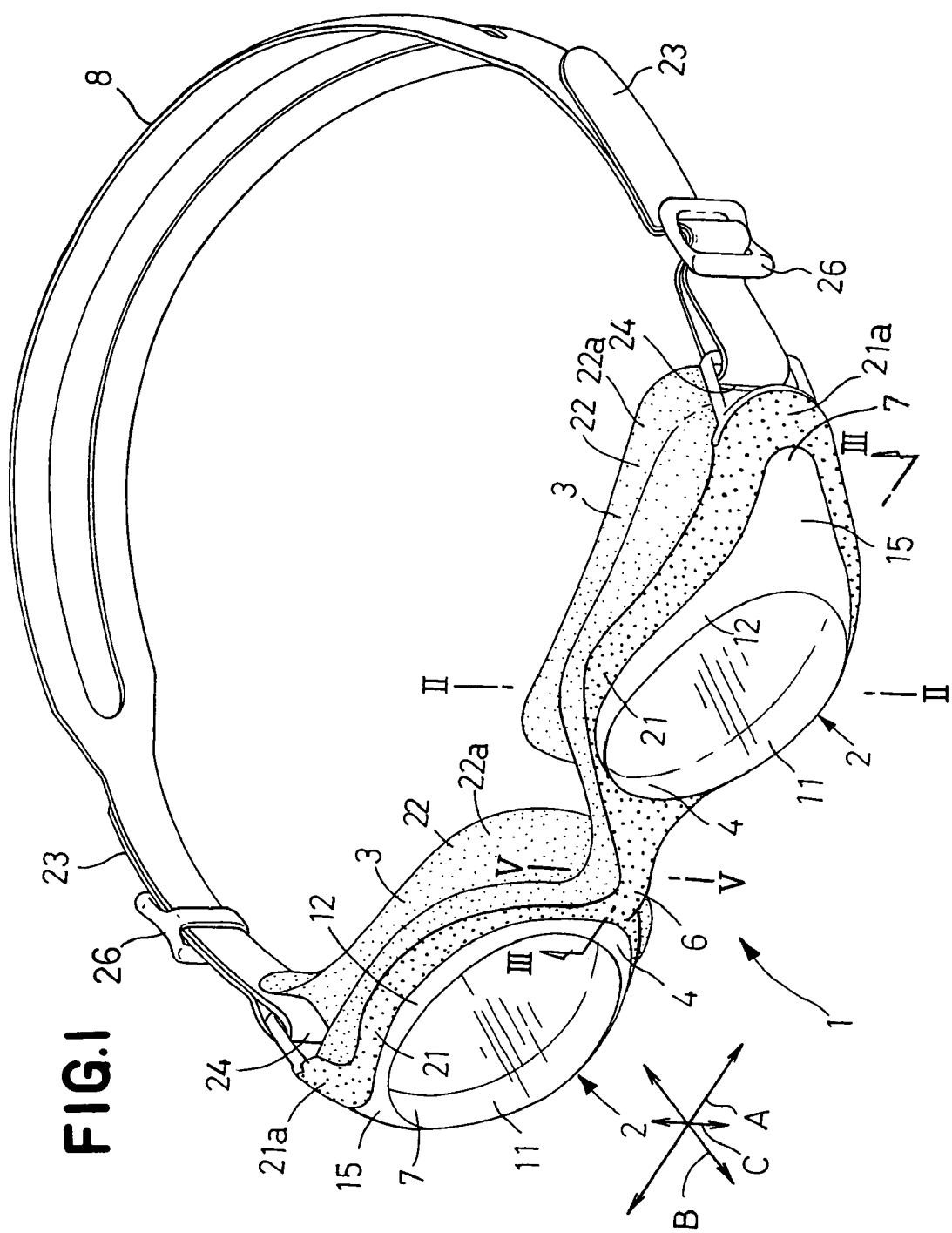
FIG. 1 is a perspective view swimming goggles.

Swimming goggles illustrated by FIG. 1 in a perspective view include a pair of lens assemblies 2 each having a transverse direction indicated by a double-headed arrow A, a back-and-forth direction indicated by a double-headed arrow B and a vertical direction indicated by a double-headed arrow C, inner ends 4 facing each other in the transverse direction A and outer ends 7 opposite to the respective inner ends 4. The goggles 1 further include pad assemblies 3 attached to the respective lens assemblies 2, a bridge 6 formed integrally with the respective pad assemblies 3 and extending between the inner ends 4 of the respective lens assemblies 2 and a head strap assembly 8 extending between the outer ends 7 of the respective lens assemblies 2.

Each of the lens assemblies 2 is made of hard and transparent plastic material and comprises, in the illustrated embodiment, an oval lens 11 and a peripheral frame 12 surrounding the lens 11. The peripheral frame 12 includes a rear extension 15 extending toward the head strap assembly 8 and this rear extension 15 defines the outer end 7 of this lens assembly 2.

Each of the pad assemblies 3 is formed by a first elastic member 21 made of a first elastic material 21a and a second elastic member 22 made of a second elastic material 22a. Referring to FIG. 1, the first elastic member 21 is indicated by a plurality of large dots and the second elastic member 22 is indicated by a plurality of small dots. The first elastic material 21a is stiffer, more elastic and correspondingly less deformable than the second elastic material 22a. The second elastic material 22a, on the other hand, has a sufficiently high flexibility and a sufficiently low elasticity to be easily deformed in conformity with a contour of the wearer's face.

Bridge 6 is formed by the first and second elastic members 21a, 22a so that the first and second elastic members 21, 22 of the respective pad assemblies 3 may become contiguous to each other. These first and second elastic materials 21a, 22a may be controllably combined to adjust a stiffness of the bridge 6 to an appropriate value.

The head strap assembly 8 has its longitudinally opposite end portions 23 passed through slits 24 formed in the rear extensions 15 of the respective lens assemblies 2 from behind the goggles 1 and then folded back. The head strap assembly 8 is formed by elastomer and elastically stretchable. While it is elastically stretchable, it is also possible to use respective buckles 26 to achieve a desired length-adjustment.

Figure 2:
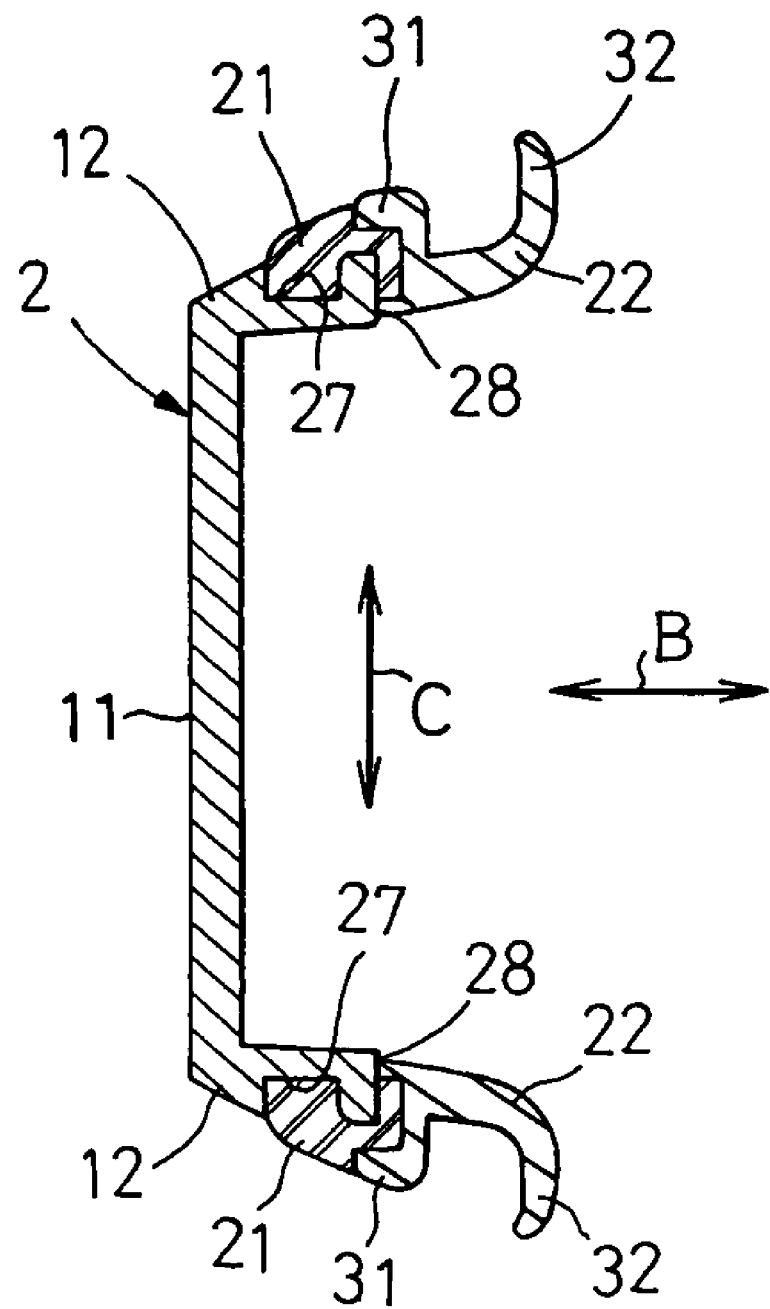
FIG. 2 is a sectional view taken along the line II—II in FIG. 1.

FIG. 2 is a sectional view taken along the line II—II in FIG. 1. Each of the lens assemblies 2 has a cup-like shape defined by the lens 11 and the peripheral frame 12 extending rearward from the lens 11 toward the wearer's face. The peripheral frame 12 is formed on its outer surface with a groove 27 making a substantially full circle of the peripheral frame 12. The first elastic member 21 has an annular shape (See FIGS. 1 and 3) and is press fitted into the groove 27. The first elastic member 21 is in close contact with and non-detachably bonded to the peripheral frame 12 in a radial direction of the lens assembly 2 including the transverse direction A and the vertical direction C. The first elastic member 21 is in close contact with and non-detachably bonded also to a part of a rear end surface 28 of the peripheral frame 12. The second elastic member 22 also is annular (See FIGS. 1 and 3) and has a front portion 31 and a rear portion 32 as viewed in the back-and-forth direction B. The rear portion 32 presents J- or inverted J-shaped curvature. The front portion 31 is in close contact with and non-detachably bonded to the first elastic member 21 in the vertical direction C as well as in the back-and-forth direction B. The front portion 31 is non-detachably bonded also to the rear end surface 28 of the lens assembly 2. The rear portion 32 presenting the J- or inverted J-shaped curvature is smoothly deformed without uncomfortably compressing the wearer's face as the rear portion 32 comes in contact with the wearer's face.

Figure 3:
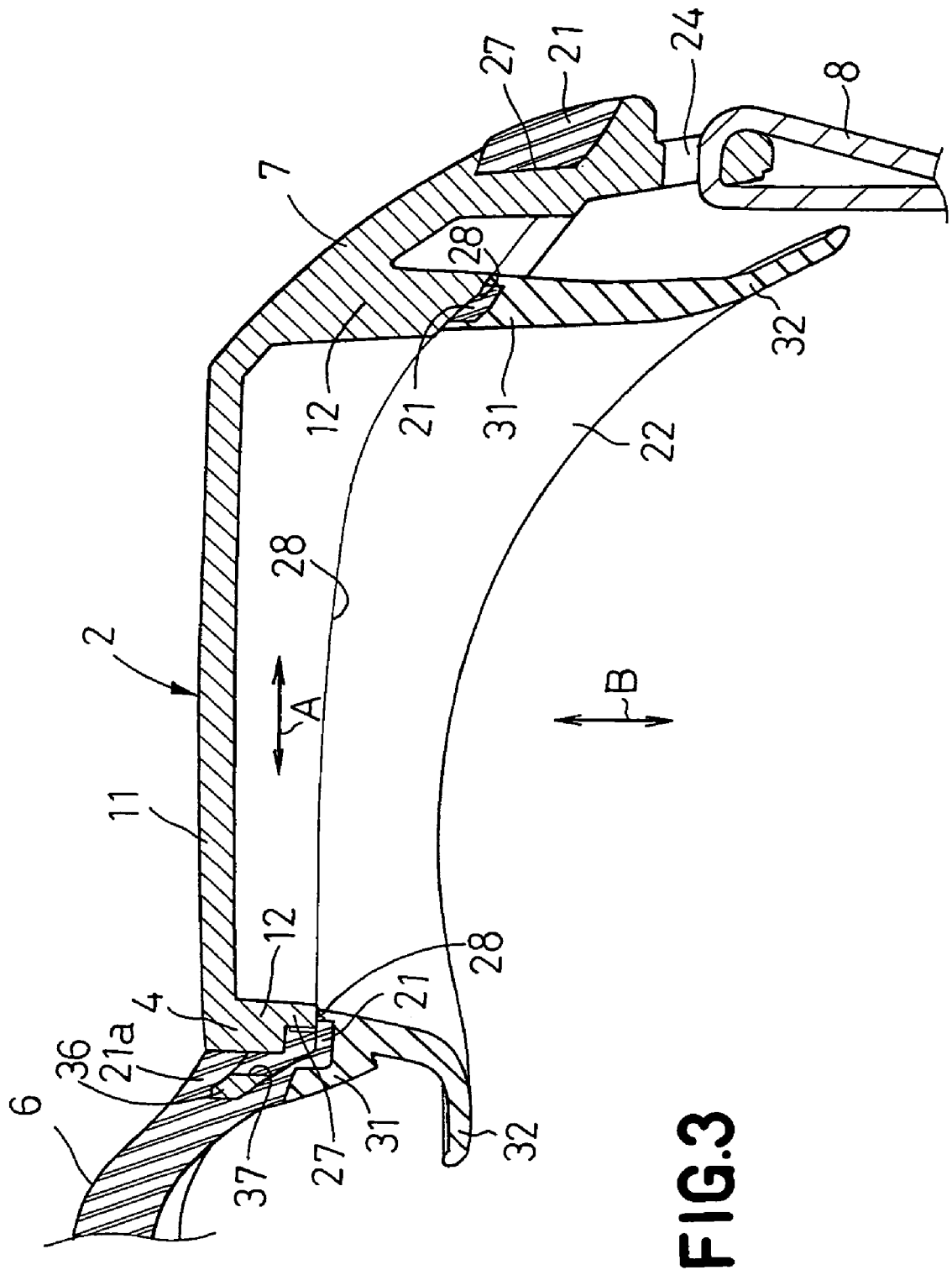
FIG. 3 is a sectional view taken along the line III—III in FIG. 1.
Figure 4:
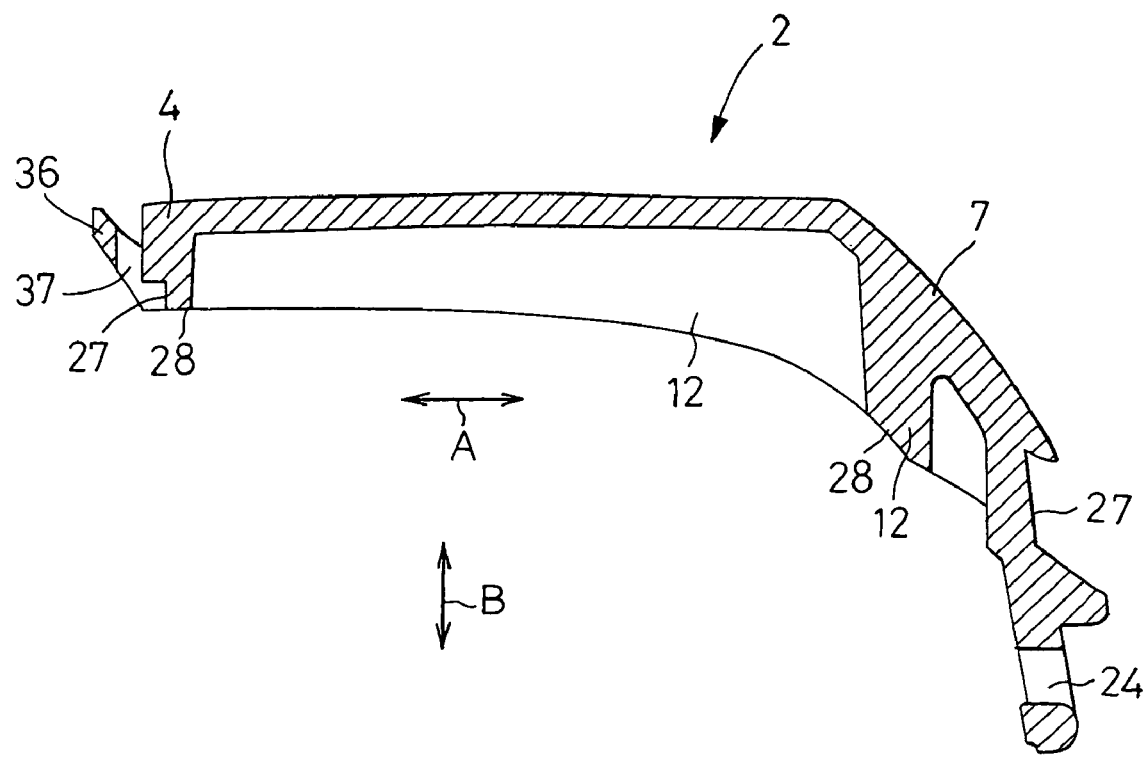
FIG. 4 is sectional view of a lens assembly in FIG. 3.

FIG. 3 is a sectional view taken along the line III—III in FIG. 1 and FIG. 4 is sectional view exclusively illustrating the lens assembly 2 appearing in FIG. 3. Referring to FIG. 4, the peripheral frame 12 of the lens assembly 2 is formed on its inner end 4 with a front extension 36 extending toward the bridge 6 and this front extension 36 is formed with a through-hole 37. The groove 27 extending along the peripheral frame 12 is continuous with the through-hole 37. While the reference numeral 27 appears in the vicinity of the through-hole 37 in FIG. 4 as if the groove 27 is formed in the through-hole 37 also, it should be understood that the groove 27 is not formed in the through-hole 37. The rear extension 15 of the peripheral frame 12 is formed with the slit 24 for passing-through of the head strap 8 and the groove 27 for press-fitting of the first elastic member 21 thereinto. In the vicinity of the inner end 4 of the lens assembly 2, the first elastic material 21a forming the first elastic member 21 is in close contact with and non-detachably bonded to the peripheral frame 12 in the transverse direction A of the lens assembly 2 so as to fill up the through-hole 37 and extends to the bridge 6 so as to cover the front extension 36, as will be apparent from FIG. 3. The first elastic member 21 is press-fitted into the groove 27 along the peripheral frame 12 so as to extend from the inner end 4 to the outer end 7 and non-detachably bonded to a part of the rear end surface 28 of the peripheral frame 12.

The second elastic member 22 has its front portion 31 being in close contact with and non-detachably bonded to the first elastic member 21 in the transverse direction A as well as in the back-and-forth direction B and non-detachably bonded also to a part of the rear end surface 28 of the peripheral frame 12, as will be apparent from FIG. 3. The second elastic member 22 bonded to the rear end surface 28 in this manner presents an annular shape extending around the peripheral frame 12. The rear portion 32 of the second elastic member 22 presents the J-shaped curvature facilitating the rear portion 32 to come in close contact with the wearer's face.

Figure 5:
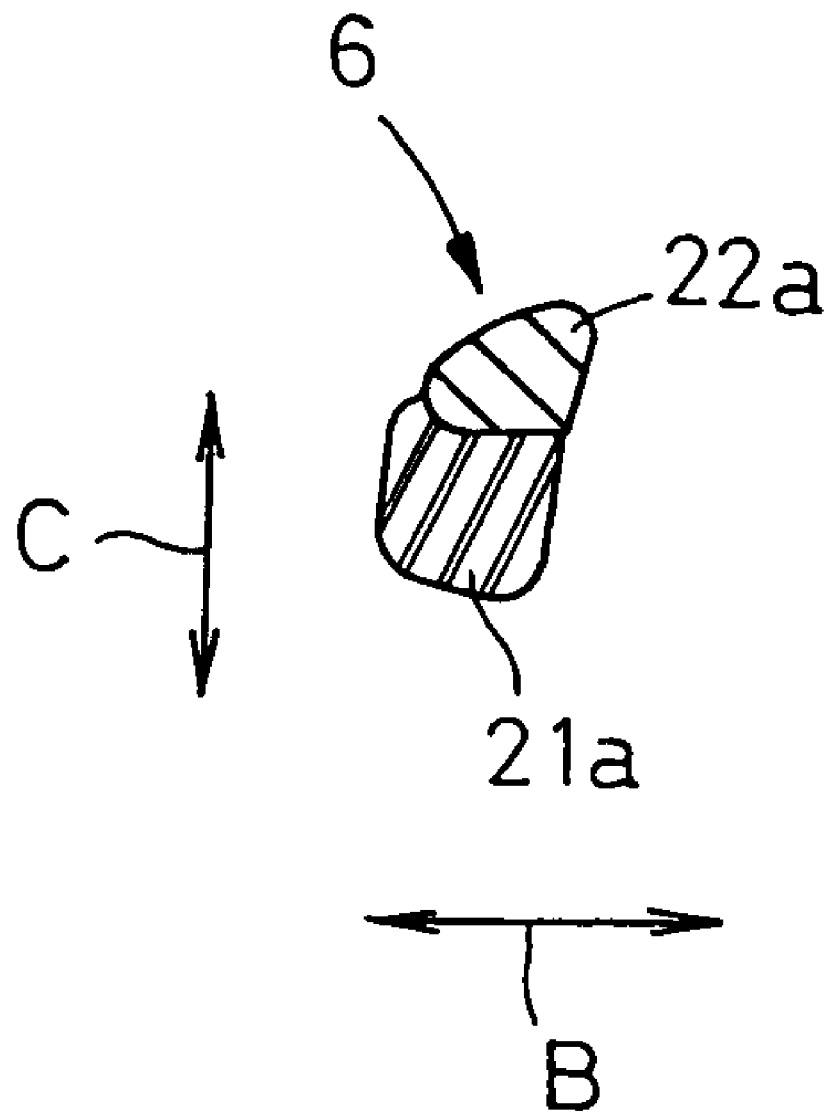
FIG. 5 is a sectional view taken along the line V—V in FIG. 1.

FIG. 5 is a sectional view taken along the line V—V vertically extending through the bridge 6 in FIG. 1. The bridge 6 is formed by non-detachably bonding the first and second elastic materials 21a, 22a to each other. The first elastic material 21a is relatively stiff and defines the first elastic member 21 and the second elastic material 22a is relatively flexible and defines the second elastic member 22 respectively in each of the pad assemblies 3. As viewed in FIG. 5, the second elastic material 22a defines an upper portion of the bridge 6 and placed aside rightward, i.e., toward the wearer's face with respect to the first elastic material 21a. Stiffness of such bridge 6 can be adjusted by appropriately selecting an area ratio of these two elastic materials 21a, 22a in the cross section of the bridge 6 and thereby it is possible to eliminate a possibility that the bridge 6 might compress the wearer's nose during use of the goggles.

Now a process for making the goggles 1 of the above-described construction will be described. After the lens assemblies 2 have been obtained by injection molding of thermoplastic material, thermoplastic elastomer as the first elastic material 21a is injection-molded to form the first elastic members 21 in desired regions of the respective lens assemblies 2. Then thermoplastic elastomer as the second elastic material 22a is injection-molded to form the second elastic members 22 in desired regions of the respective lenses as well as in desired regions of the respective first elastic members 21. The second elastic material 22a is non-detachably welded to the lens assemblies 2 and the first elastic members 21 which come in contact with the second elastic material 22a. In the pad assemblies 3, the first elastic members 21 made of the relatively stiff first elastic material 21a are non-detachably bonded to the respective lens assemblies 2 in an effective manner. More specifically, even if the second elastic members 22 made of the relatively flexible second elastic material 22a are significantly deformed as the goggles 1 are worn, such deformation leads neither to corresponding deformation of the first elastic members 21 nor to separation of the first elastic members 21 and the respective lens assemblies 2 one from another. On the other hand, the relatively deformable second elastic members 22 are in close contact with and non-detachably welded to the respective first elastic members 21 in the back-and-forth direction B as well as in the radial direction of the respective lens assemblies 2. As one of measures allowing the second elastic members 22 to be reliably bonded to the respective first elastic members 21, it may be conceived to enlarge a contact area, i.e., a welded area between these first and second elastic members 21, 22. However, enlargement of the area over which these two elastic members 21, 22 are in close contact and welded to each other in the back-and-forth direction B of the respective lens assemblies 2 would lead to enlargement of outer diameters of the lens assemblies 2 and the pad assemblies 3. Enlargement of the outer diameters of the lens assemblies 2 and the pad assemblies 3 would cause a frictional resistance of water to increase. In the goggles 1 according to the illustrated embodiment, on the contrary, the second elastic members 22 are in close contact with and welded to the respective first elastic members 21 also in the radial direction of the respective lens assemblies 2, i.e., not only in the back-and-forth direction B of the respective lens assemblies 2 but also in a thickness direction of the respective pad assemblies 3. In this way, the contact area between the first and second elastic members 21, 22 can be enlarged without enlarging the outer diameters of the lens assemblies 2 and the pad assemblies 3. In such goggles 1, any significant deformation of the second elastic members 22 leads neither to separation between the second elastic members 22 and the respective first elastic members 2 nor to separation between the first elastic members 21 and the respective lens assemblies 2. In addition, it is possible for the goggles 1 to reduce the outer diameters of the respective pad assemblies 3 and thereby to alleviate a frictional resistance of water experienced by the wearer as he or she swims.

The present invention may be implemented also by preparing the bridge 6 separately of the pad assemblies 3 as well as of the lens assemblies 2, instead of forming the bridge 6 integrally with the pad assemblies 3, and attaching this bridge 6 to the pad assemblies 3 and the lens assemblies 2. Alternatively, instead of molding the pad assemblies integrally with the lens assemblies 2, the lens assemblies 2 may molded independently of the lens assemblies 2 and then the pad assemblies 3 may be elastically deformed to attach them to the lens assemblies 2, preferably using suitable adhesive or welding technique. It should be noted here that, in such separately prepared pad assemblies 3, the first and second elastic members 21, 22 may be integrally injection-molded. Preferably, natural rubber or thermoplastic elastomer having a stiffness in a range of 40 to 90 as measured by "Spring-Operated Stiffness Test A" prescribed by Clause 5.2 of JIS K 6301 is used as the first elastic material 21a and natural rubber or thermoplastic elastomer having a stiffness in a range of 10 to 40, more specifically having a stiffness lower than that of the first elastic material 21a by at least 20 is used as the second elastic material 22a.

The present invention may be implemented by incorporating, in addition to the feature that the first and second elastic members 21, 22 are different in stiffness, a feature that these first and second elastic members 21, 22 are different also in color tone and/or chemical composition. With the first and second elastic members 21, 22 being different in color tone, the goggles 1 will be aesthetically colorful. Phrase used herein "different in chemical composition" means that the first and second elastic members 21, 22 are made of different types of elastomer, for example, made of silicon rubber and urethane rubber, respectively.

The present invention allows for production of the swimming goggles characterized in that the elastic materials are non-detachably bonded to each other to form the pad without increasing the frictional resistance of water.

What is claimed is:

1. Swimming goggles having a vertical direction, a transverse direction orthogonal to said vertical direction and a back-and-forth direction orthogonal to both said vertical direction and said transverse direction, said swimming goggles comprising:
    a pair of cup-shaped lens assemblies arranged side by side in said transverse direction;
    annular pad assemblies attached to peripheral frames of respective said lens assemblies and extending in said back-and-forth direction;
    a bridge extending between inner ends of respective said lens assemblies opposed to each other;
    a strap band assembly between outer ends of respective said lens assemblies;
    said lens assemblies being formed from a hard plastic material and each of said pad assemblies being formed from two types of elastic material of which the one defines a first elastic member non-detachably attached to each of said peripheral frames and the other defines a second elastic member non-detachably bonded to said first elastic member and adapted to come in close contact with face of a swimmer wearing said swimming goggles; and
    said first elastic member being formed from first elastic material and in close contact with and non-detachably bonded to said lens assembly in a radial direction of said lens assembly and in said back-and-forth direction, with said second elastic member being formed from second elastic material differing from said first elastic material in stiffness and any one of color tone and chemical composition and in close contact with and non-detachably bonded to said first elastic member in said radial direction and said back-and-forth direction.

2. The swimming goggles according to claim 1, wherein said second elastic material is more flexible than said first elastic material.

3. The swimming goggles according to claim 1, wherein said bridge is formed by said first elastic material and said second elastic material, both of which extending between the inner end of each of said pad assemblies.

4. The swimming goggles according to claim 3, wherein said second elastic material defines the upper portion of said bridge and is placed towards a wearer's face with respect to said first elastic material.

* * * * *